United States Patent [19]

Rogowski

[11] Patent Number: 5,684,707
[45] Date of Patent: Nov. 4, 1997

[54] APPARATUS AND METHOD FOR ANALYZING PAPER SURFACE TOPOGRAPHY

[75] Inventor: Donald Frank Rogowski, Covington, Va.

[73] Assignee: Westvaco Corporation, New York, N.Y.

[21] Appl. No.: 514,622

[22] Filed: Aug. 11, 1995

Related U.S. Application Data

[63] Continuation-in-part of Ser. No. 316,792, Oct. 3, 1994, abandoned.
[51] Int. Cl.$^6$ .............................. G06F 19/00; D21F 7/06
[52] U.S. Cl. .............................. 364/471.03; 364/471.02; 162/198; 73/159
[58] Field of Search ........... 364/469.01, 471.01–471.03, 364/472.06, 472.1, 472.12, 552, 560, 572, 563; 73/159; 382/108, 141; 356/371, 429–431, 237; 162/DIG. 10, DIG. 11, 252, 253, 262, 263, 198

[56] References Cited

U.S. PATENT DOCUMENTS

| | | | |
|---|---|---|---|
| 4,669,300 | 6/1987 | Hall et al. | 73/105 |
| 4,692,210 | 9/1987 | Forrester | 162/49 |
| 4,752,897 | 6/1988 | Zoeller et al. | 364/550 |
| 4,888,983 | 12/1989 | Dunfield et al. | 73/104 |
| 4,914,309 | 4/1990 | Masaharu et al. | 250/572 |
| 4,965,736 | 10/1990 | Balakrishnan | 364/471.03 |
| 5,122,963 | 6/1992 | Chen | 364/471.03 |
| 5,358,606 | 10/1994 | Makkonen | 162/198 |

FOREIGN PATENT DOCUMENTS

| | | | |
|---|---|---|---|
| 0464958 | 8/1992 | European Pat. Off. | G01N 33/34 |
| 57-74601 | 5/1982 | Japan | G01B 5/00 |
| 60-135708 | 7/1985 | Japan | G01B 21/00 |
| 62-75209 | 4/1987 | Japan | G01B 21/08 |
| 4-65619 | 3/1992 | Japan | G01B 21/00 |

OTHER PUBLICATIONS

Form Talysurf Series "Form and Surface Texture Measurement", The Queens Award for Technical Achievement 1992, Rank Taylor Hobson 291–24E/0895 CS 20m. Printed in Eng.

"Multidimensional Digital Signal Processing," by D.E. Dudgeon and R.M. Mersereau, Prentice–Hall, Inc. Englewood Cliffs, New Jersey, 1984, pp. 28–33, 113–127.

"Measuring Fabric Mark in Board Using Image Analysis," by A.A. Koukoulas et al., *Journal of Pulp and Paper Science*, vol. 20, No. 8, pp. 220–225, Aug. 1994.

Fourier Analysis of Surface Roughness, by M. Brock, pp. 3–45, and "News from the Factory," pp. 46–49, Technical Review, Surface Roughness Analysis, No. 3, 1983, *Bruel & Kjaer Instruments Inc.* ISSN 007–2621.

"The effect of basestock structure on coating weight distribution," by H. Tomimasu, K. Suzuki and T. Ogura, and Philip Luner, *Tappi Journal*, Coating, May 1990, pp. 179–187.

M.A.MacGregor & T.E. Conners, Image Analysis of an LWC Paper Reveals Wire Mark in the Print Density Variations, *TAPPI Proceedings*, 1987 Engineering Conference, pp. 661–667.

(List continued on next page.)

*Primary Examiner*—Reba I. Elmore
*Assistant Examiner*—Steven R. Garland
*Attorney, Agent, or Firm*—J. R. McDaniel; R. L. Schmalz

[57] ABSTRACT

This invention relates to an apparatus and method for identifying periodic roughness variations on a paper surface. Such devices of this type, generally, collect topography data from the paper surface, analyze the data, and compare the data with known signature topographies of paper machine clothing and equipment to determine the location in the paper manufacturing process where the periodic roughness variations on the paper surface are being produced.

6 Claims, 7 Drawing Sheets

OTHER PUBLICATIONS

S.J.I'Anson & H.W. Kropholler, "Enhancing Visibility of Wire–Mark by Image Analysis," *Journal of Pulp and Paper Science*, vol. 17, No. 1, Jan. 1991, pp. J22–J26.

The SCAPA Group, "Unaform Forming Fabrics . . . " etc. advertisement and Stephan I'Anson, Detection of periodic marks in paper and board by Image analysis, *Pulp and Paper Journal*, Dec. '93 (Circle 122) and pp. 72–76.

A. A. Koukoulas, N. Nguyen & B.D. Jordan, "Measuring Fabric Mark in Board Using Imgae Analysis", *Journal of Pulp and Paper Science*, vol. 20, No. 8, Aug. 94 pp. J220–J225.

APPARATUS AND METHOD FOR ANALYZING PAPER SURFACE TOPOGRAPHY

CROSS-REFERENCE TO RELATED APPLICATIONS

This application is a continuation-in-part of the commonly assigned, U.S. patent application Ser. No. 08/316,792 filed Oct. 3, 1994, entitled APPARATUS AND METHOD FOR ANALYZING PAPER SURFACE TOPOGRAPHY, now abandoned.

BACKGROUND OF THE INVENTION

1. Field of the Invention

This invention relates to an apparatus and method for identifying periodic roughness variations on a paper surface. Such devices of this type, generally, collect topography data from the paper surface, analyze the data, and compare the data with known signature topographies of paper machine clothing and equipment to determine the location in the paper manufacturing process where the periodic roughness variations on the paper surface are being produced.

2. Description of the Related Art

As applied to paper, "print quality" is a subjective, human eye assessment of a particular paper surface respective to the printed product of that surface. One of the more influential objective factors bearing upon the print quality of a paper surface is the "roughness" of that surface. Additionally, paper is also subjectively appraised for simply unprinted visual surface smoothness. Consequently, numerous methods have been devised to measure the roughness of an unprinted paper surface as a predictor of the printed product.

Several widely used, indirect, methods of paper surface roughness measurement, characterized as Sheffield smoothness, Bekk smoothness and Parker Print Surf, include air leak techniques which measure the volume of air that leaks, over a fixed time interval, between the paper surface and a test equipment seal, or, conversely, the time required for the leakage of a fixed air volume. Although these indirect surface roughness measurement methods offer a numerically quantified, relative value of surface roughness, they have not proven to be consistent, reliable indicators of print quality.

Traditional surface roughness measurement relies upon the single, line trace of a stylus over the surface as is represented by U.S. Pat. No. 4,888,983 to L. G. Dunfield et al. Surface height values are measured at uniformly separated increments within a single, vertical evaluation plane. Such surface height values are digitized and processed algorithmically by Dunfield et al to determine a corresponding print quality index.

Machine made paper, however, has a directional orientation relative to the machine production line. A greater percentage of papermaking fiber aligns with the machine direction than with the cross-machine direction. Extremely exaggerated, this circumstance of machine direction fiber alignment may be perceived as a corrugated topography. If measured by a single, vertical displacement stylus in a direction transversely of the corrugation ribs, the analysis would report a "rough" surface with large but highly regular vertical distance variations between the measured peaks and valleys. When measured in a direction parallel with the corrugation ribs, the analysis would report a "smooth" surface with small variations between vertical distance variations. Only by means of three dimensional measurement may the parallel ribbed nature of surface be recognized. Exemplary of such prior art is commonly assigned U.S. patent application Ser. No. 08/010,760 to D. F. Rogowski entitled "Apparatus and Method for Measuring Paper Surface Roughness".

From the foregoing illustration, it is demonstrated that a three dimensional topography is defined by length, width and height coordinates, the length and width coordinates being in the same plane and the height coordinate measured perpendicularly from the length/width plane.

Often, the "visual smoothness" of both unprinted and printed paper are influenced by patterns in the roughness. Patterns in paper tend to be easily observed in paper and in situations where a "smooth" paper is desired, this is considered an undesirable situation. Therefore, the simplest approach to rectifying this situation is to make a change in the manufacturing process of the paper so as to cause the pattern to no longer occur in the paper. One difficultly with this approach is that unless the pattern can be positively identified, it will be difficult to know which parts of the manufacturing process need to be altered in order to eliminate the pattern from the paper.

The eye is generally not a good tool for trying to positively identify the source of the pattern although it can observe them. Some of the reasons for this is that the patterns that are observed in paper are often subtle, there may be more than one pattern in the paper, and the various manufacturing operations that can introduce patterns into a paper can have very similar but distinct patterns that the eye is not able to distinguish. As a result of these situations, it is desirable to have a repeatable, non-subjective method for identifying patterns that are present in paper.

As an example of the concern about the presence of a pattern in paper, the article "Measuring Fabric Mark in Board Using Image Analysis" by A. A. Koukoulas, N. Nguyen, and B. D. Jordan, Journal of Pulp and Paper Science: Vol. 20 No. 8, pages J220–J225 is noted. Koukoulas et al. describe a method for evaluating the relative strength of a pattern whose origin in the paper manufacturing process is known.

The relative strength of the pattern in paper samples is determined by applying the two-dimensional Fourier transformation to optical data collected from the paper samples. A limitation of the work presented by Koukoulas et al. is that although they present a method from measuring the relative strength of a pattern whose origin in the paper manufacturing process is provided, no means of identifying the source of patterns whose origin in the paper manufacturing process is unknown. The method presented by Koukoulas et al. is also severely limited in that it cannot be applied to the identification of the sources of patterns in roughness since the Koukoulas et al. method requires the paper sample to be in intimate contact with a prism which is only possible by deforming the surface of the paper by pressing the paper sample against a prism with pressure using a hydraulic press.

It is apparent from the above that there exists a need in the art for a paper surface analyzing system which is capable of accurately measuring the paper surface roughness profile but which at the same time can determine at which point in the paper manufacturing process periodic roughness variations are being introduced on the paper surface. It is a purpose of this invention to fulfill these and other needs in the art in a manner more apparent to the skilled artisan once given the following disclosure.

SUMMARY OF THE INVENTION

Generally speaking, this invention fulfills these needs by providing a method for analyzing a surface profile of paper produced by a papermaking machine having papermaking components, comprising the steps of: preparing a sample paper sheet by the papermaking machine; collecting topography data of the sample paper sheet; collecting topography data of the papermaking components; analyzing the topography data of the sample paper sheet and the papermaking machine components; comparing the topography data of the sample paper sheet and the papermaking machine components; identifying, if any, process component signatures in the topography data of the sample paper sheet which correlate to the topography data of the papermaking machine components; and adjusting, if necessary, papermaking components to eliminate the processing component signatures in the topography data of the sample paper sheet.

In certain preferred embodiments, the topography data of the sheet is collected and a determination of a two-dimensional frequency spectrum is made. Also, the topography data of the papermaking machine components is collected directly from the papermaking machine components or through the use of foil impressions of the components and the determination of a two-dimensional frequency spectrum is made.

In another further preferred embodiment, periodic patterns in the surface roughness of the paper sample can be identified so that corrective action can be taken to eliminate the patterns.

The preferred paper surface analyzing system, according to this invention, offers the following advantages: excellent papermaking machine component surface measuring characteristics; excellent paper surface measuring characteristics; excellent papermaking process component signature identifying characteristics; good stability; good durability; ease of use; and good economy. In fact, in many of the preferred embodiments, these factors of component and paper surface measuring characteristics and process component signature identification are optimized to an extent that is considerably higher than heretofore achieved in prior, known paper surface analyzing systems.

The above and other features of the present invention, which will become more apparent as the description proceeds, are best understood by considering the following detailed description in conjunction with the accompanying drawings, wherein like characters represent like parts throughout the several views and in which:

DETAILED DESCRIPTION OF THE INVENTION

EQUIPMENT

Figure 1:
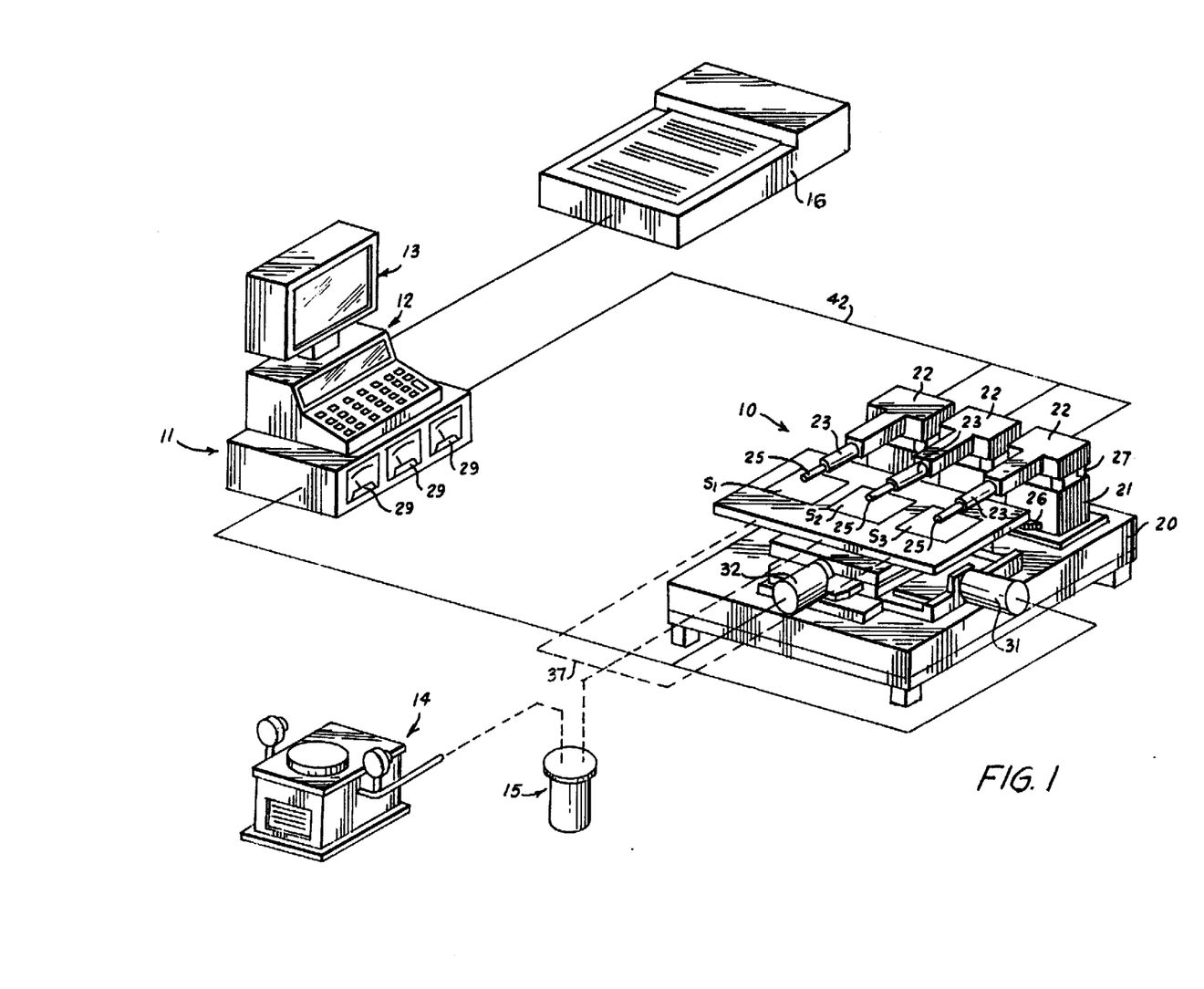
FIG. 1 is a pictorial schematic of the invention physical components.

The basic structural components of the present invention are illustrated pictorially by FIG. 1 to include the cooperative assembly of a sample survey unit 10, a digital data processing computer 11, a keyboard control console 12, a monitor 13, a vacuum pump 14, a regulated vacuum reservoir 15 and a printer 16.

The sample survey unit 10 comprises a massive support table 20 having one or more stylus support units 21. Each support unit carries a vertically adjustable stylus head 22 which supports a rigid stylus arm 23. The stylus per se 25 may be an article such as described in detail by U.S. Pat. No. 4,669,300 issued Jun. 2, 1987 to P. H. Hall et al. Typical stylus specifications would include a 0.0001 inch/2.53 µm diamond point radius for use on "fine" or writing paper and a 0.010 inch/0.25 mm carbide ball point radius for bleached paperboard.

Manual rotation of a jack wheel 26 causes a vertical displacement of the stylus head 22 within guide tubes 27 to calibrate the stylus 25 midpoint relative to the plane of a sample sheet $S_1$, $S_2$, or $S_3$.

Each sample sheet S is secured to the surface of a Cartesian coordinate table 30 (FIG. 4) by means of a vacuum system. Translational movement of the table 30 is directed by the computer 11 acting upon stepper motors 31 and 32. Upon a signal from the computer, one or both motors 31 or 33 will respond to the stepper motor driver 33 (FIG. 2) with a predetermined angle of rotation to translate the position of table 30 in mutually perpendicular directions under the stylus arms 23 to trace a transversely progressing series of parallel paths, each path having a predetermined number of stop point positions at regular spacings to define a grid pattern of equidistantly separated survey measuring points as illustrated by the trace pattern of FIG. 3. In the presently preferred embodiment of the invention, a grid of 128 parallel paths, each 3.2 inches long, spaced over a 3.2 inch distance are each provided with 128 survey data points along respective 3.2 inch lengths, i.e. $(128)^2$ equidistantly spaced data points or a grid of 256 parallel paths, each 1.6 inches long, spaced over a 1.6 inch distance are each provided with 256 survey data points along respective 1.6 inch lengths, i.e. $(256)^2$ equidistantly spaced data points.

The spacing of these data points may be changed to resolve frequency ranges descriptively characteristic of the roughness scale under examination. The maximum frequency that can be resolved is equal to one-half the data point spacing frequency.

To secure the position of thin light weight samples such as paper, the Cartesian coordinate table 30 is provided with one or more vacuum sinks 35 (FIG. 4) covered by a porous metal plate 36 that has been machined to a specified flatness. The plate 36 pore size is selected to allow air to move through the plate without deforming the sample into the pore sinks. An example is a 10 micron pore size metal gas filter plate machined to a flatness of ±0.001 inches from Mott Metallurgical Corp., Farmington, Conn.

Figure 4:
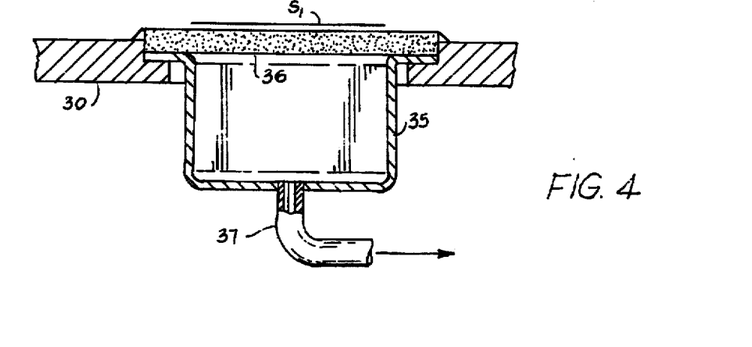
FIG. 4 is a sectioned detail of the invention sample mounting apparatus.

Below the plate 36, the sink 35 is evacuated by a conduit system 37 connected to a vacuum source such as a pump 14. However, within the conduit system 37, between the sink 35 and the pump 14, is provided a regulated vacuum reservoir 15 sized to dampen any vacuum pulsations originating from the vacuum source.

Figure 2:
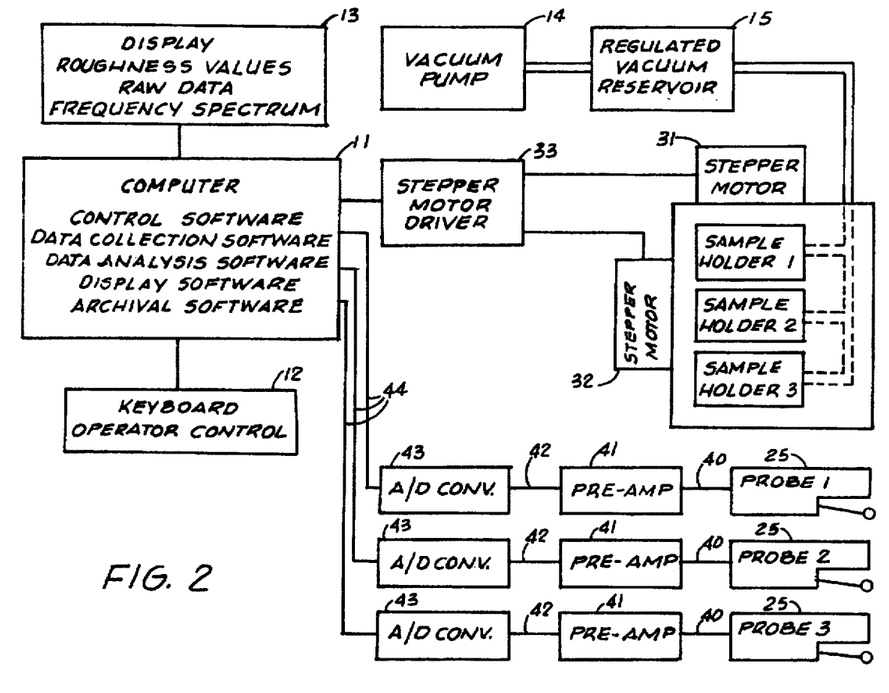
FIG. 2 is a line and block schematic of the invention.

To complete the system's physical description relative to FIG. 2, each analog signal 40 of stylus 25 is amplified by a power boosting preamplifier circuit 41. The amplified stylus analog signal 42 is subsequently transmitted to an analog-to-digital conversion circuit 43 for the production of corresponding digital data signals 44 in a suitable response form of computer 11.

ROUGHNESS AND VISUAL ASSESSMENTS

A sheet roughness determination procedure begins with placement of one or more sample sheets $S_1$, $S_2$ or $S_3$ on respective sample holders 36 of table 30 (FIG. 4). The stylus displacement probes 25 are placed onto the sample surfaces by manual manipulation of jack wheels 26 and adjusted to the mid-point of the probe displacement range.

Figure 3:
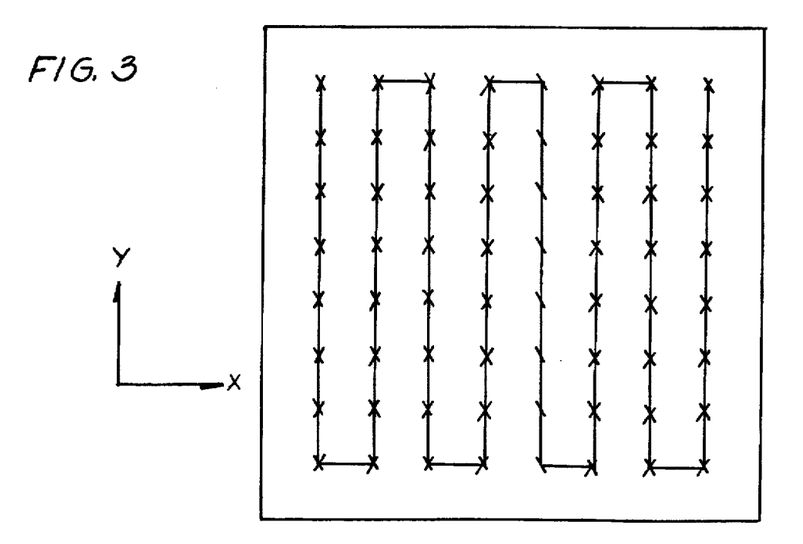
FIG. 3 is a trace pattern of the invention sample table movement.
Figure 5:
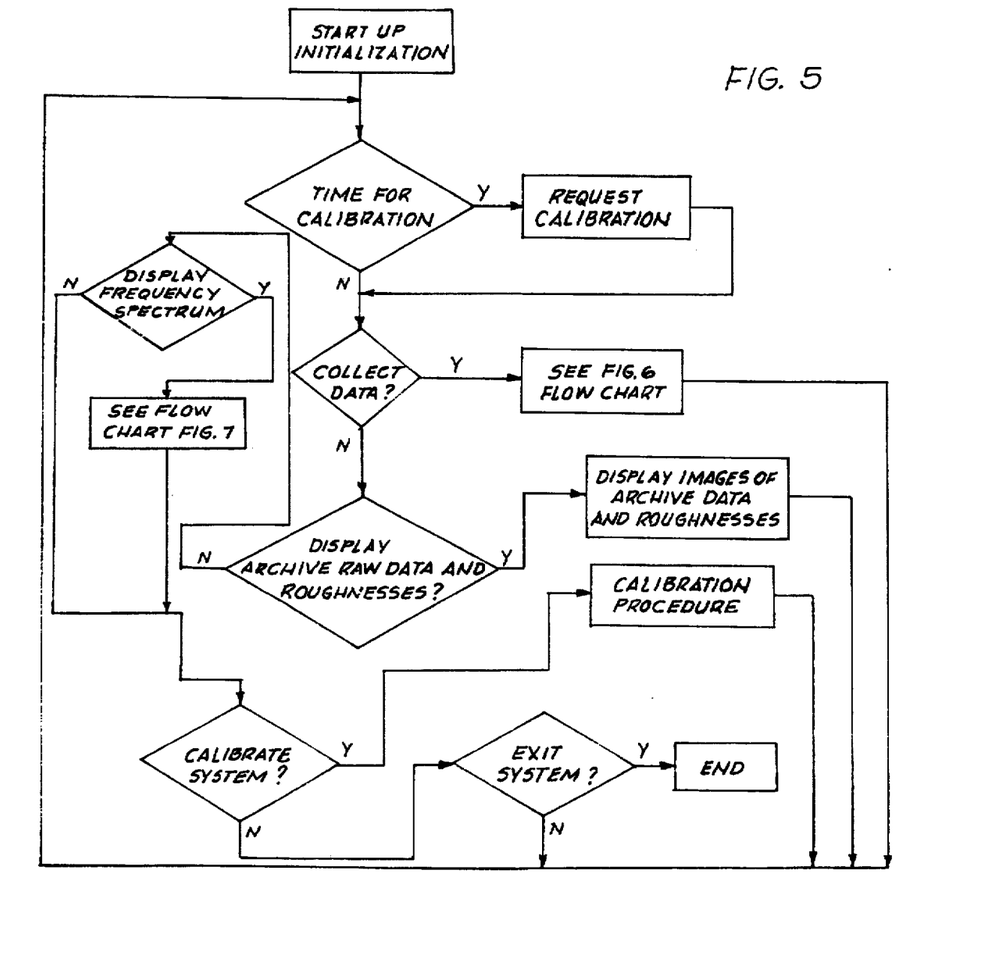
FIG. 5 is a block flow chart of the computer software control program applicable to the invention.
Figure 6:
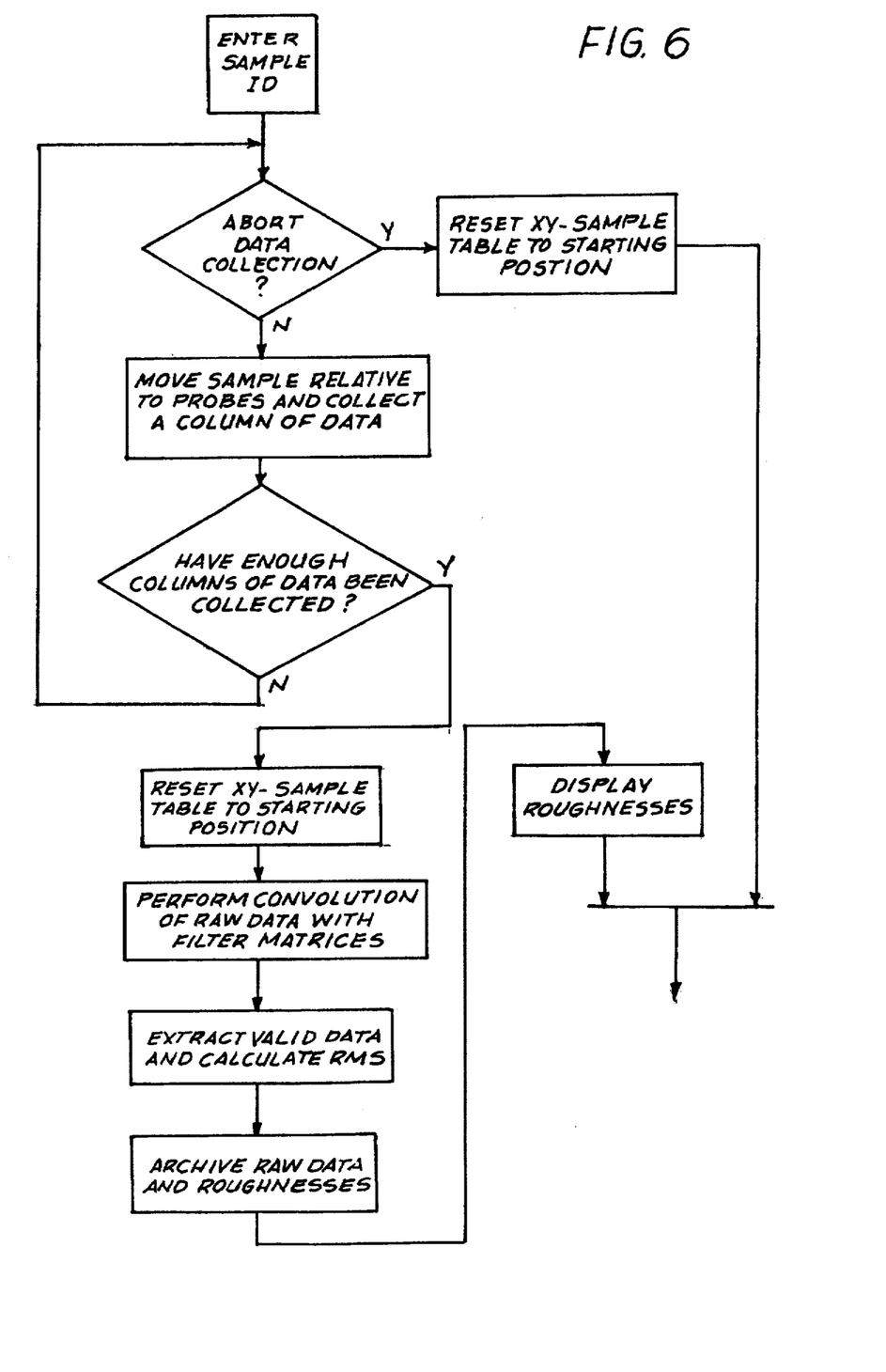
FIG. 6 is a block flow chart of the data analysis subroutine for roughness determination referenced in the flow chart of FIG. 5.

With reference to the software function flow chart of FIGS. 5 and 6, survey data collection begins with movement of Cartesian coordinate table 30 along the prescribed FIG. 3 path, giving pause at each data point to minimize the presence of mechanical movement noise in the signal system. The digital values produced by the A/D converters 43 (FIG. 2) are stored in correspondence with their respective matrix address. This process is repeated until the prescribed data course is completed.

Those of ordinary skill in the art will recognize that the stylus type of measuring device described herein may be alternatively replaced by a laser beam measuring device.

Upon completion of the raw data matrix set, the correspondingly stored data is convoluted with a two-dimensional, finite-extent impulse response (FIR), or nonrecursive, zero-phase band-pass, digital filter that has been multiplied by a window function such as a circular Kaiser window. Alternatively, the raw data may be convoluted as accumulated and then stored for further or subsequent processing. The FIR filter that has been multiplied with the window was constructed and stored in the computer memory before the data collection procedure. Resultantly, the filter/window combination is retrieved from the memory for convolution. The FIR filter and window are designed using standard mathematical procedures that are described in "Multidimensional Digital Signal Processing" by D. E. Dudgeon and R. M. Mersereau, Prentice-Hall, 1984, pages 29–31 and pages 118–124. The choice of the filter cut off parameters is based upon the scale of roughness that one is interested in quantifying. The quantified scale of roughness is dependent upon the subjective quality of property one is attempting to quantify. Implementation of the convolution process is described by Dudgeon and Mersereau at pages 113–118.

The resultant matrix for each convolution of the raw data will contain both "good" and "bad" data. The "good" data is extracted from the resultant matrix of each convolution and then the root-mean-square roughness of this "good" data is determined and presented to the operator via the monitor 13 display or a printer 16 (FIG. 1).

Those of ordinary skill in the art will recognize that the root-mean-square roughness parameter for calculating a roughness value described herein may be alternatively replaced by another roughness parameter such as roughness average.

To describe this mathematical manipulation more graphically, the raw data represented by the relative height values at the matrix measuring points may be reduced to a single, root-mean-square value. However, this value does not usually correspond with the subjective evaluations of artists and experts. To derive a root-mean-square value for a specific type of paper that does correspond with the subjective evaluations of experts, a statistically sufficient number of unprinted and printed examples on samples of a specific paper type are comparatively graded by experts. Necessarily, this will be a subjective, visual, manual grading. Unprinted and printed examples of the same specific paper type are evaluated by the present invention to identify a subcomponent surface with a constituent surface frequency or frequency spectrum that, when reduced to a root-mean-square value, corresponds with the subjective evaluation of experts. Once the relevant frequency or spectrum is identified for a specific type of paper, all subsequently produced quantities of this specific paper type may be graded by the root-mean-square value of the sub-component surfaces with that frequency range.

Regressing, the data matrix representing a raw sample surface within the test area is mathematically restructured into several constituent surface simulations; each conforming to a particular surface profile frequency within a spectrum of such particular frequencies. Collectively, the full frequency spectrum of such surface simulations add up to the original, raw data surface.

Convoluted upon this spectral range of surface simulations is a mathematical filter derived from the references given above. By this model, selected surface frequencies or subspectrum are isolated from the whole surface spectrum for comparative relevance to subjective manual appraisals. Thereby, a signature frequency or subspectrum is identified for subsequent application to any example of the analyzed paper type.

For the presently preferred embodiment of the invention, raw data for each sheet sample is convoluted two or three times, each time with a different filter. Other embodiments may convolute the raw data with fewer or more filters and thus produce fewer or more roughness values with one roughness value being determined for each filter used in a convolution.

FREQUENCY SPECTRA

The present invention can be used to generate a frequency spectrum of surface variations in the collected topography data. A frequency spectrum of a surface contains information about the amplitude or magnitude of sine wave-surfaces that are used to mathematically characterize a surface which allows the identification or recognition of period variations or patterns in the topography.

Figure 7:
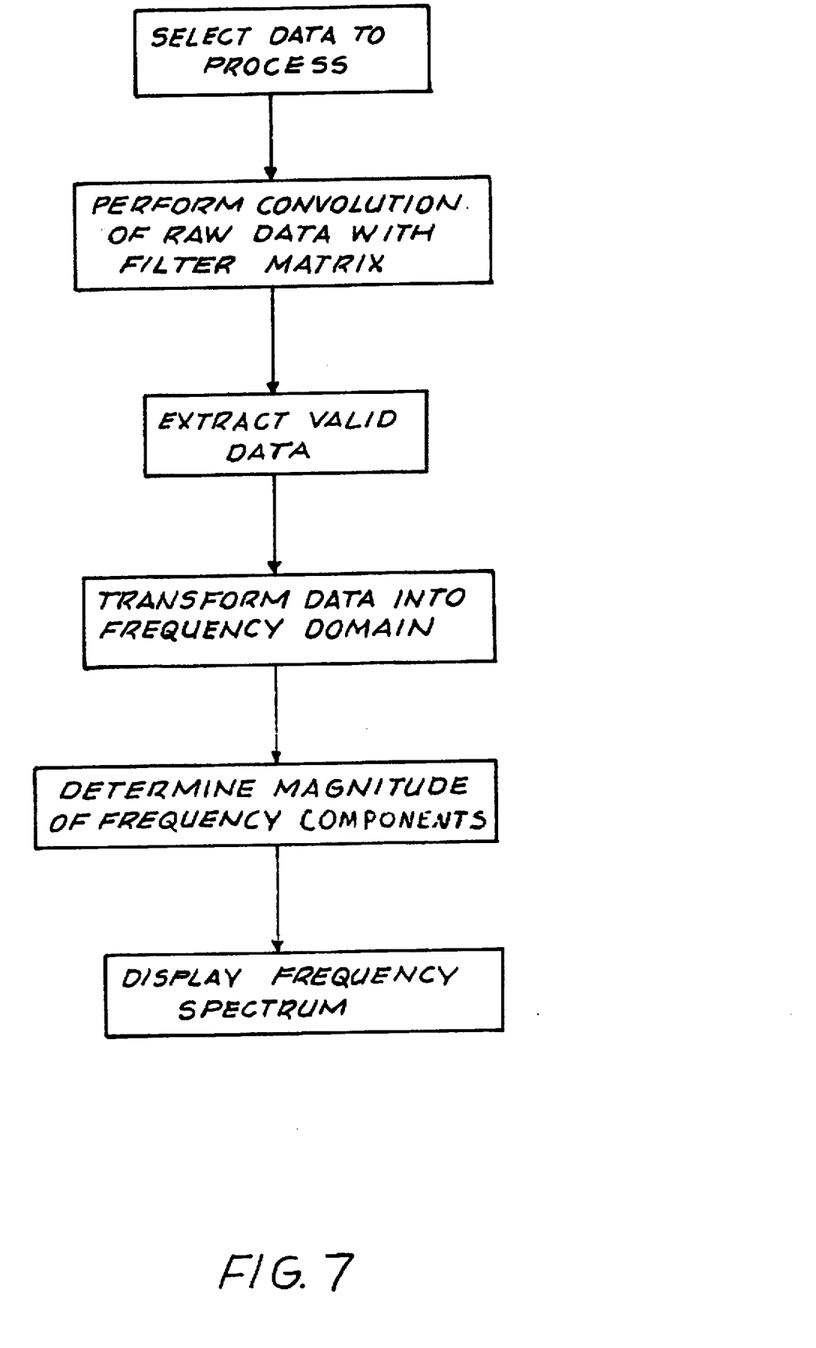
FIG. 7 is a block flow chart of the data analysis subroutine for frequency spectrum determination referenced in the flow chart of FIG. 5.

As shown in FIG. 7, upon completion of the raw data matrix with the previously described preferred embodiment, the correspondingly stored data can be mathematically transformed to yield the two-dimensional frequency spectrum of the corresponding data or it may be convoluted with a two-dimensional, finite-extent impulse response (FIR) or a nonrecursive, zero-phase band-pass digital filter that has been multiplied by a window function prior to its transformation to yield the two-dimensional frequency spectrum if it is desired to exclude certain frequencies from the spectrum. The mathematical transformation is accomplished with the use of the 2-dimensional fast-fourier transform followed by the determination of the magnitude of the values resulting from the 2-dimensional fast-fourier transform.

Figure 8:
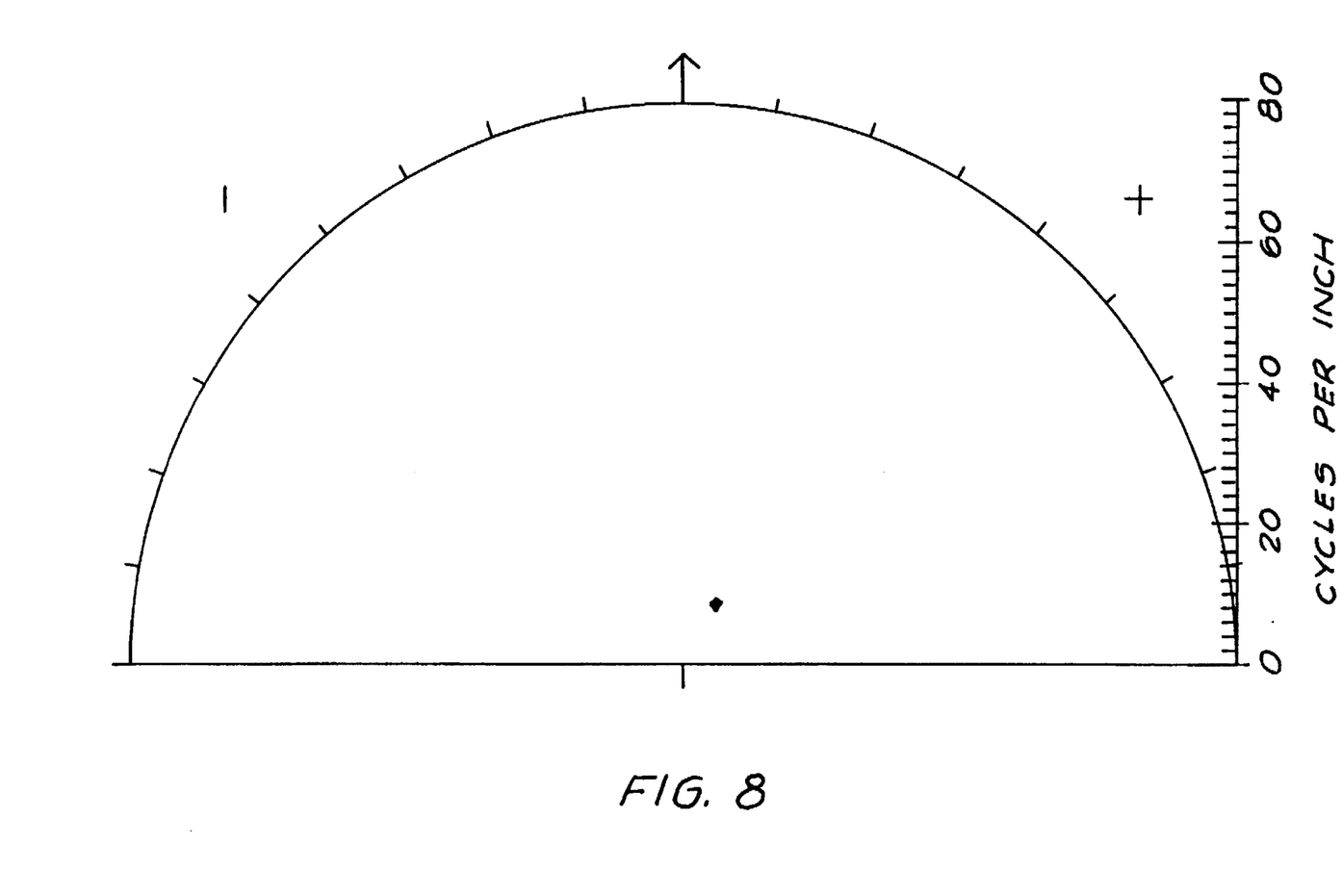
FIG. 8 is an illustration of a frequency spectrum, according to the present invention.

As an introduction to the use and interpretation of a frequency spectra, a simple frequency spectrum will be examined. FIG. 8 is an example of a simple frequency spectrum. The frequency components that are present in each surface occur within and on the borders of the half circle of FIG. 8. An examination of the frequency spectrum of FIG. 8 reveals that it contains a single significant frequency component.

Figure 9:
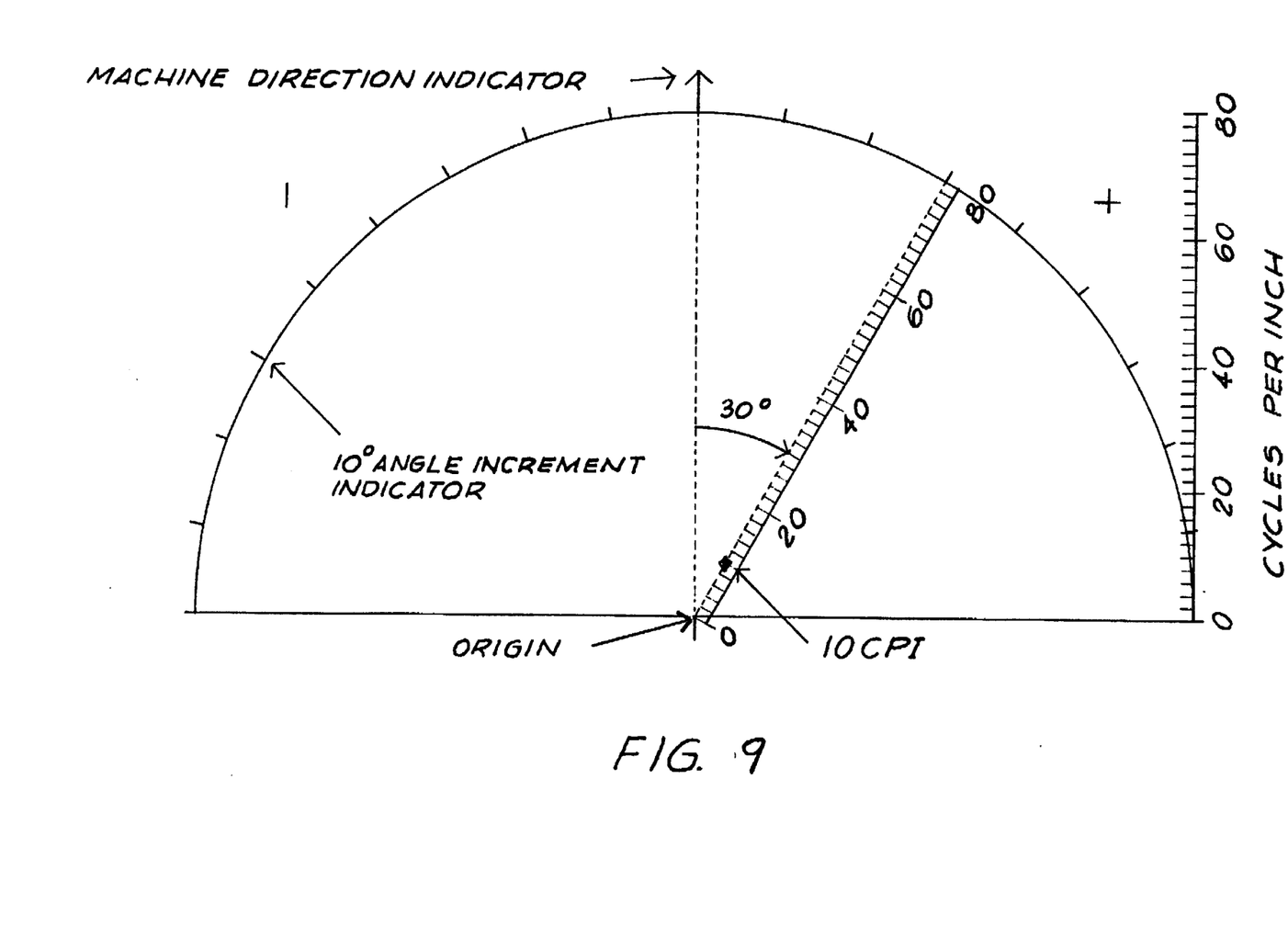
FIG. 9 is an illustration of the frequency spectrum of FIG. 8 with additional labeling, according to the present invention.

To facilitate the discussion of interpreting frequency spectra, the frequency spectrum of FIG. 8 is presented again in FIG. 9 with labeling that is not part of the normal frequency spectrum presentation.

A key feature of frequency spectra is that they are polar. That is, the frequency components in a spectrum are described by their distance from an origin on the semi-circle and their angle relative to a reference direction. The frequency of a component is determined by measuring the distance from the origin to the location of the component and comparing the distance with the scale at the right hand side of the frequency spectrum. The angle of a component is determined by measuring the angle between the vertical ray on the semi-circle, which indicates the machine direction, and the frequency component. Angles to the right of the machine direction are described as positive angles and angles to the left of the machine direction are described as negative angles. The plus and minus signs outside of the half circle are reminders about the sign of an angle. For convenience, marks at 10 degree spacings from the machine direction are placed along the border of the half circle.

The single frequency component displayed in FIG. 9 has a frequency of 10 cycles per inch and an angle of +30° indicating the presence of a periodic surface variation with a frequency of 10 cycles per inch and a direction of travel of 30° to the right of the machine direction.

The absolute angle of a frequency component relative to the machine direction is dependent upon the orientation of the samples on the Cartesian coordinate table 30 (FIG. 4). The relative angle between frequency components does not depend upon sample orientation.

Those of ordinary skill in the art will recognize that the frequency spectrum presented as in FIGS. 8 and 9 may be alternatively presented in a full circle or a "complete" frequency spectrum presentation, in which the magnitude of the frequency spectrum data is presented twice.

In addition to frequency and direction information, frequency spectra contain information about the amplitude of sine wave-surfaces that are used to mathematically characterize a surface. Information about amplitudes or magnitudes as a function of frequency and direction are presented as topographic maps in the frequency spectra. This depiction results in large amplitude (strong) frequency components appearing as relatively large "dots" due to many tightly spaced contour lines that are drawn at the location of the frequency components in the frequency spectrum. Thus, the strength of a component is indicated by the relative diameter of the component in the topographic presentations of the frequency spectra.

The strength of magnitude information of a component can be used to determine the relative strength or prominence of a pattern in a paper surface. By monitoring the magnitude of the frequency components of process signatures in a paper surface, it is possible to determine the effectiveness of modifications to the paper manufacturing process that are aimed at reducing or eliminating a pattern in a paper surface. If there is more than one pattern in a paper surface, the relative magnitudes of components can be used to determine the relative prominence of the patterns in a paper surface. The relative magnitudes of components due to a single pattern can also yield insight into the mechanism of the transference of the pattern from the process component to the paper surface.

Those of ordinary skill in the art should recognize that the information contained in two-dimensional frequency spectra may be presented in a variety of presentation forms and that this information tells much about the paper manufacturing process.

With respect to the identification of the paper manufacturing process that introduced the periodic variation of pattern in the paper surface, the primary usefulness of a frequency spectrum comes not from examining the spectrum of a sample by itself, but rather in comparing the spectrum of a sample to the spectra or signatures of machine process components, for example drilled or grooved rolls and machine clothing. The positive identification of the source of a pattern in a paper surface allows manufacturing process modifications to be made to eliminate the pattern and to some degree, reduce sheet roughness.

The identification of the source of patterns in paper samples involves the generation of the frequency spectra or signatures of the paper manufacturing process components and the generation of the frequency spectra of the paper samples. The generation of frequency signatures associated with machine components begins with the making of aluminum foil impressions of the machine component surfaces. Preferably, aluminum or other suitable foil impressions of machine components are obtained under simulated operating conditions to obtain patterns of the paper manufacturing components as they would be imparted to the paper on the paper making machine. Aluminum foil impressions are processed using the surface analyzer (10, 11, 12, 13, 14, 51 and 16 in FIG. 1). Also, paper samples produced by the same machine components are measured using the same surface analyzer (10, 11, 12, 13, 14, 15 and 16 in FIG. 1). The frequency spectra of the aluminum foil impressions are the frequency signatures of the corresponding machine components. By comparing the frequency spectra of paper samples to frequency signatures of machine components, the source of patterns in a paper sample can be identified with paper manufacturing processes. Once the source of the pattern is determined, alternatives can be explored to reduce or eliminate the undesired pattern.

Those of ordinary skill in the art should recognize that the frequency signatures of some paper manufacturing process components may be obtained from process components by directly measuring the topography of a representative sample of the component such as may be done with dryer fabric clothing, for example.

Although the idea behind pattern identification is straightforward, the identification of patterns by spectra comparisons requires care, insight, and a knowledge of the paper making process. Paper machine dynamics affect how component signatures are transferred to samples. Paper machine component signatures can be partially obscured by background frequencies or distorted by sheet stretching and shrinking. Only part of a component signature may be transferred to a sheet under certain machine operating conditions. Different paper machine components may have identical signatures in which case it may not be possible to pin point a single source. Also, a paper sample may have more than one pattern in it. A pattern whose source is on one side of the paper web may be transferred to the opposite side. All of these situations result in the pattern identification process being more involved than the roughness measurement process.

IMAGE ENHANCEMENT

One method of presenting surface data collected with the surface analysis technique of the present invention, is the gray-scale image. In a gray-scale image, the surface elevations of the data collected with the present invention are converted to an black and white image intensity or gray-scale. In the present embodiment, higher elevations correspond to lighter shades of gray and lower elevations correspond to darker shades of gray, although one skilled in the art could easily recognize that other elevation to image intensity correspondences could exist. However, in gray-scale images of raw or filtered data from paper samples, it is often difficult to observe the patterns that are indicated by the components of the frequency spectra. The ability to visually observe the patterns indicated by the components of the frequency spectra is desirable since a paper sample may contain more than one manufacturing process signature. It is also desirable to be able to visually present, as in a gray-scale image, how the identified process signature appears in a sample to allow a confirmation of which of the identified process signatures was the cause of the undesired pattern observed with the eye in the paper sample. It is for these situations that the image enhancement capability of the surface analysis technique of the present invention has been developed.

One reason that it is difficult to identify patterns in gray-scale images of raw or filtered data of paper is that unless the patterns are dominant, the patterns can be obscured by "random" variations in the topography data. Thus, if gray-scale images of topography data are to be used to examine patterns, the patterns in paper topography data must be made dominant relative to the "random" variations in the data. This process is referred to as pattern or image enhancement.

The mathematical approach to pattern enhancement involves two steps: filtering the data to retain only the frequency components of interest, those of a single paper manufacturing component, and making the retained frequency components of interest very strong relative to the retained frequency components that are not of interest. The mathematical procedures for this image enhancement process are presented by the previously discussed Dudgeon and Mersereau publication, pages 124–126. Following pattern enhancement, a gray-scale image of the enhanced data is generated.

The first step of image enhancement begins with an examination of the frequency spectrum of the sample. The frequency range of the components that are to be retained and enhanced is determined. The choice of the frequency range is very important and requires insight. Almost all machine component frequency signatures contain at least two frequency components, and often times more than two frequency components. If an enhanced image is to be generated that is to have a reasonable chance of resembling the machine component pattern, as many as possible of the frequency components that are part of the signature must be included in the frequency range to be retained and enhanced. However, if the range is too inclusive, noise will be retained and enhanced along with the desired frequency components and this will result in poor image enhancement. Another factor that impacts the quality of enhanced gray-scale images is the retention of high frequency components. High frequency components are needed to give an enhanced image crispness. However, the crispness of the image must be balanced with the need to prevent the quality of the enhanced image from being diminished due to extraneous components that occur at high frequencies. Often, the optimal frequency range to retain and enhance is found by a trial and error examination of the resulting enhanced images.

Once a frequency range is selected, a band-pass filter is designed that will retain the desired frequencies and eliminate the undesired frequencies. The raw data is then filtered. After filtering, the pattern in the filtered data is enhanced by multiplying each frequency component of the filtered data by its magnitude raised to a power. The choice of the power controls the degree of the enhancement. Generally, in the current embodiment, a power of two provides good enhancement. This enhancement process causes the dominant frequency components to become more dominant and yields an enhanced image of the dominant frequency components that is free from significant distortion. This process enhancement is based on the relative strength of a frequency component. The relative strength issue is addressed by the selection of the frequency range of the band-pass filter.

One skilled in the art can recognize that with a certain degree of accuracy, a comparison of the enhanced gray-scale image of the frequency components from an unknown paper manufacturing process component to the actual paper manufacturing process components can lead to an identification of the paper manufacturing process component that introduced the periodic surface variation onto the paper surface.

Once given the above disclosure, many other features, modifications or improvements will become more apparent to the skilled artisan. Such features, modifications or improvements are, therefore, considered to be a part of this invention, the scope of which is to be determined by the following claims.

What is claimed is:

1. A method for analyzing a surface profile of paper produced by a papermaking machine having papermaking components, comprising the steps of:

preparing a sample paper sheet by said papermaking machine;

physically collecting two-dimensional topography data of said sample paper sheet;

physically collecting two-dimensional topography data of said papermaking components;

analyzing said topography data of said sample paper sheet and said papermaking machine components, wherein said step of analyzing said topography data of said sample paper sheet and said papermaking machine components is further comprised of the step of: determining frequency spectra of said topography data of said sheet and said components by determining frequency, magnitude, and angle information of said topography data of said sample paper sheet and said papermaking machine components;

comparing said analyzed topography data of said sample paper sheet and said papermaking machine components;

identifying, if any, process component signatures in said topography data of said sample paper sheet which correlate to said topography data of said papermaking machine components from said comparison of said analyzed data; and adjusting, if necessary, papermaking components to eliminate said processing component signatures in said topography data of said sample paper sheet.

2. The method, as in claim 1, wherein said step of collecting topography data of said papermaking components is further comprised of the step of:

making foil impressions of said papermaking components such that said impressions substantially represent a topography of said papermaking components.

3. The method, as in claim 1 wherein said step of analyzing said topography data of said sample paper sheet is further comprised of the step of:

identifying periodic process component signatures which are located substantially in said sample paper sheet.

4. The method, as in claim 1, wherein said step of analyzing said topography data of said sample paper sheet and said papermaking machine components is further comprised of the step of:

determining a frequency range of topography data of said sheet and said components to be retained and enhanced;

filtering said topography data of said sheet and said components; and enhancing said process component signatures in said topography data of said sheet and said components.

5. The method, as in claim 4, wherein said enhancing step is further comprised of the step of:

preparing a gray-scale image of said topography data of said sheet and said components.

6. The method, as in claim 1 wherein said analyzing step is further comprised of the step of:

by measuring a distance of a frequency component from an origin on a complete frequency spectrum presentation and an angle of said frequency spectra relative to a reference direction.

* * * * *